(12) United States Patent
Beeckler et al.

(10) Patent No.: US 11,911,094 B2
(45) Date of Patent: *Feb. 27, 2024

(54) HEAT TRANSFER THROUGH A CATHETER TIP

(71) Applicant: Biosense Webster (Israel) Ltd., Yokneam (IL)

(72) Inventors: Christopher Thomas Beeckler, Brea, CA (US); Joseph Thomas Keyes, Sierra Madre, CA (US); Assaf Govari, Haifa (IL); Yigal Ultchin, Rehovot (IL); Meir Bar-tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 767 days.

This patent is subject to a terminal disclaimer.

(21) Appl. No.: 15/990,532

(22) Filed: May 25, 2018

(65) Prior Publication Data

US 2019/0357972 A1 Nov. 28, 2019

(51) Int. Cl.
*A61B 18/14* (2006.01)
*C25D 5/00* (2006.01)
(Continued)

(52) U.S. Cl.
CPC .......... *A61B 18/1492* (2013.01); *C25D 5/10* (2013.01); *C25D 5/611* (2020.08);
(Continued)

(58) Field of Classification Search
CPC ........ B41J 2202/18; A61B 2018/00077; A61B 2018/00083; A61B 2018/00351; A61B 2018/00011; A61B 18/1492; A61B 5/6869

See application file for complete search history.

(56) References Cited

U.S. PATENT DOCUMENTS

| | | | | |
|---|---|---|---|---|
| 4,532,924 A | * | 8/1985 | Auth | A61B 18/14 606/50 |
| 6,241,724 B1 | * | 6/2001 | Fleischman | A61N 1/0565 606/41 |

(Continued)

FOREIGN PATENT DOCUMENTS

| | | |
|---|---|---|
| EP | 3238646 A2 | 11/2017 |
| EP | 3315087 A1 | 5/2018 |

(Continued)

OTHER PUBLICATIONS

Extended European Search Reported dated Sep. 30, 2019, from European Appl. No. 19176437.2.

(Continued)

*Primary Examiner* — Thomas A Giuliani
*Assistant Examiner* — Christine A Dedoulis
(74) *Attorney, Agent, or Firm* — Troutman Pepper Hamilton Sanders LLP

(57) ABSTRACT

Described embodiments include an apparatus that includes a flexible electrically-insulating substrate, including an inner surface and an outer surface, and shaped to define (i) multiple narrower channels passing between the inner surface and the outer surface, and (ii) one or more wider channels passing between the inner surface and the outer surface. The apparatus further includes an outer layer of an electrically-conducting metal covering at least part of the outer surface, an inner layer of the electrically-conducting metal covering at least part of the inner surface, a plating layer of the electrically-conducting metal that plates the wider channels such as to connect the outer layer to the inner layer, and respective columns of the electrically-conducting metal that fill the narrower channels such as to connect the outer layer to the inner layer. Other embodiments are also described.

15 Claims, 5 Drawing Sheets

(51) Int. Cl.
  *C25D 5/10*   (2006.01)
  *A61B 17/00*  (2006.01)
  *A61B 18/00*  (2006.01)
  *B23P 19/04*  (2006.01)

(52) U.S. Cl.
  CPC ............. *A61B 2017/00526* (2013.01); *A61B 2018/00029* (2013.01); *A61B 2018/00077* (2013.01); *A61B 2018/00083* (2013.01); *A61B 2018/00351* (2013.01); *A61B 2018/00577* (2013.01); *A61B 2018/00779* (2013.01); *A61B 2018/00821* (2013.01); *A61B 2018/00839* (2013.01); *A61B 2018/00875* (2013.01); *B23P 19/04* (2013.01)

(56) References Cited

U.S. PATENT DOCUMENTS

| | | | | |
|---|---|---|---|---|
| 7,862,563 | B1* | 1/2011 | Cosman | A61B 18/1477 606/41 |
| 8,456,182 | B2 | 6/2013 | Bar-Tal et al. | |
| 2006/0091551 | A1 | 5/2006 | Lin et al. | |
| 2009/0143651 | A1* | 6/2009 | Kallback | A61B 5/0215 600/301 |
| 2014/0336640 | A1* | 11/2014 | Beeckler | A61B 18/1492 606/41 |
| 2016/0014908 | A1 | 1/2016 | Rathbum | |
| 2017/0143414 | A1* | 5/2017 | Sliwa | A61B 18/1492 |
| 2018/0110562 | A1 | 4/2018 | Govari et al. | |
| 2019/0117296 | A1 | 4/2019 | Govari et al. | |
| 2019/0357972 | A1 | 11/2019 | Beeckler et al. | |

FOREIGN PATENT DOCUMENTS

| | | |
|---|---|---|
| EP | 3572024 A1 | 11/2019 |
| JP | 2002176263 A | 6/2002 |
| JP | 2006086358 A | 3/2006 |
| JP | 2017136356 A | 8/2017 |
| JP | 2017202306 A | 11/2017 |
| WO | 2016/130713 A1 | 8/2016 |

OTHER PUBLICATIONS

Extended European Search Reported dated Nov. 26, 2020, from European Appl. No. 20185673.9.

Notification of Reasons for Refusal dated Mar. 28, 2023, from corresponding Japanese Application No. 2019-097408.

* cited by examiner

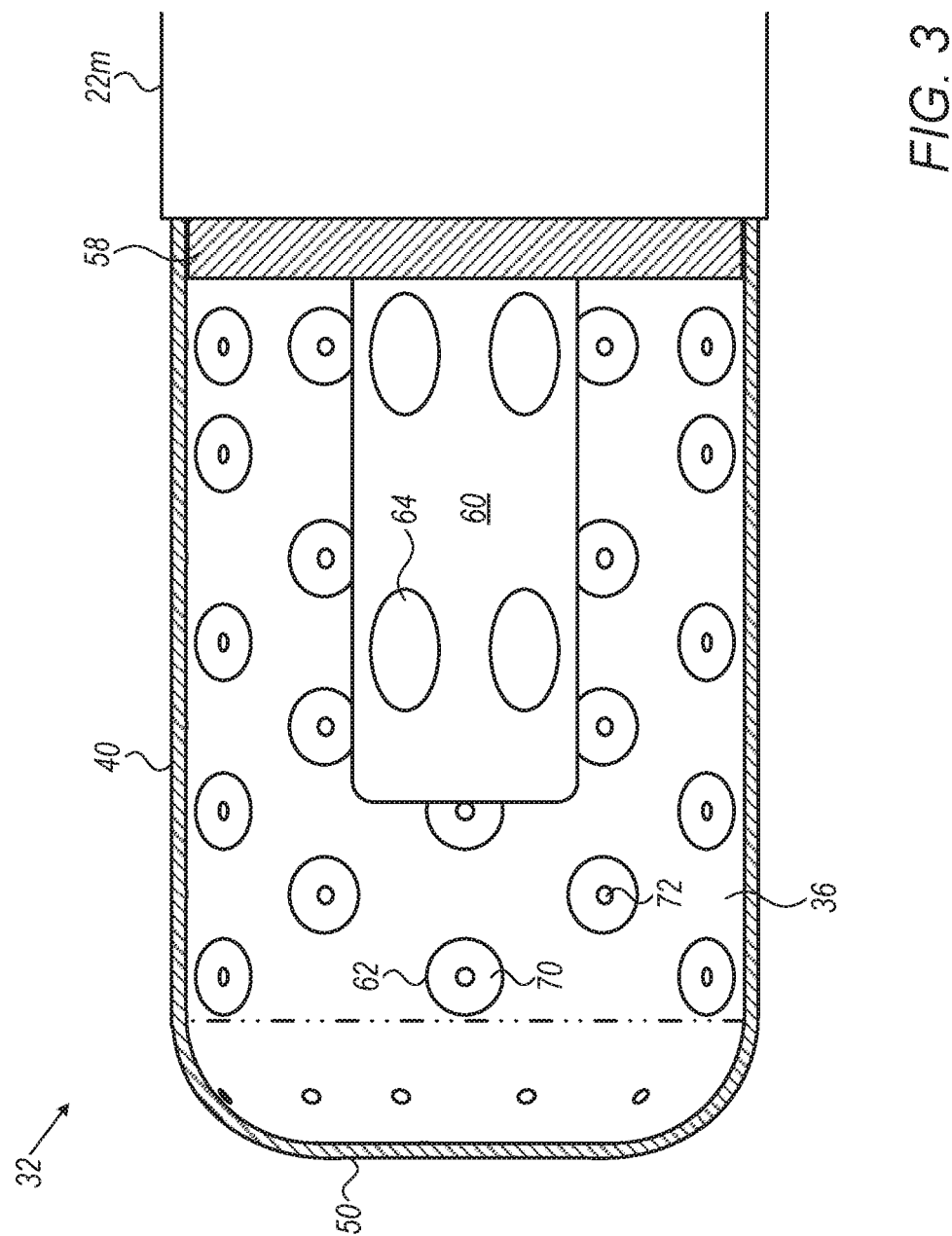

HEAT TRANSFER THROUGH A CATHETER TIP

FIELD OF THE INVENTION

The present invention is related to ablation catheters and the use thereof in ablation procedures.

BACKGROUND

In some ablation procedures, an electrode disposed at the tip of an ablation catheter is brought into contact with tissue, and radiofrequency (RF) energy is then passed from the electrode into the tissue. The RF energy raises the temperature of the tissue, thus creating lesions in the tissue.

US Patent Application Publication 2018/0110562, whose disclosure is incorporated herein by reference, describes a catheter that includes an insertion tube, a flexible substrate, and one or more electrical devices. The insertion tube is configured for insertion into a patient body. The flexible substrate is configured to wrap around a distal end of the insertion tube and includes electrical interconnections. The electrical devices are coupled to the flexible substrate and are connected to the electrical interconnections.

SUMMARY OF THE INVENTION

There is provided, in accordance with some embodiments of the present invention, an apparatus that includes a flexible electrically-insulating substrate that includes an inner surface and an outer surface and is shaped to define (i) multiple narrower channels passing between the inner surface and the outer surface, and (ii) one or more wider channels passing between the inner surface and the outer surface. The apparatus further includes an outer layer of an electrically-conducting metal covering at least part of the outer surface, an inner layer of the electrically-conducting metal covering at least part of the inner surface, a plating layer of the electrically-conducting metal that plates the wider channels such as to connect the outer layer to the inner layer, and respective columns of the electrically-conducting metal that fill the narrower channels such as to connect the outer layer to the inner layer.

In some embodiments, the substrate is shaped to define at least 1,000 narrower channels.

In some embodiments, a total area of respective outer openings of the narrower channels is at least 10% of an area of the outer surface.

In some embodiments, the electrically-conducting metal includes gold.

In some embodiments, the apparatus further includes:
at least one constantan trace disposed on the inner surface and electrically isolated from the inner layer; and
at least one gold trace disposed on the inner surface, electrically isolated from the inner layer, and covering the constantan trace at a thermocouple junction.

In some embodiments, the apparatus further includes a supporting structure bonded to the inner layer, and the substrate and the supporting structure are shaped to define an interior lumen.

In some embodiments, the substrate and the supporting structure are shaped to define a thimble that contains the interior lumen.

In some embodiments, the apparatus further includes a catheter configured for insertion into a body of a subject, and the supporting structure is coupled to a distal end of the catheter.

In some embodiments, the distal end of the catheter includes a flow diverter configured to divert fluid received from a proximal end of the catheter, and the supporting structure is coupled to the flow diverter such that the flow diverter is disposed inside of the interior lumen.

In some embodiments, an average diameter of each of the narrower channels is between 5 and 50 microns.

In some embodiments, an average narrower-channel diameter of each of the narrower channels is less than 50% of an average wider-channel diameter of each of the wider channels.

In some embodiments, a thickness of the substrate is between 5 and 75 microns.

In some embodiments, the apparatus further includes one or more electrically-conductive traces disposed on the inner surface and electrically isolated from the inner layer,
the substrate is shaped to define respective holes opposite the traces, and
the outer layer includes:
a main portion; and
one or more islands that are electrically isolated from the main portion and contact the traces, respectively, by virtue of at least partly filling the holes.

There is further provided, in accordance with some embodiments of the present invention, a method that includes inserting, into a body of a subject, a distal end of a catheter that includes a substrate having an inner surface, which is covered at least partly by an inner metallic layer, and an outer surface, which is covered at least partly by an outer metallic layer, the substrate being shaped to define (i) multiple narrower channels, which pass between the inner surface and the outer surface and are filled by metal columns, and (ii) one or more plated wider channels that pass between the inner surface and the outer surface. The method further includes, subsequently to inserting the distal end of the catheter into the body of the subject, contacting tissue of the subject with the outer metallic layer. The method further includes, while contacting the tissue, passing an electric current, via the outer metallic layer, into the tissue, such that heat is generated in the tissue and is transferred, via the metal columns, to the inner metallic layer. The method further includes evacuating the heat, from the inner metallic layer, into blood of the subject, by passing an irrigating fluid through the plated wider channels.

In some embodiments, the tissue includes cardiac tissue of the subject.

In some embodiments, the outer metallic layer includes a main portion and one or more islands that are electrically isolated from the main portion, and the method further includes, using the islands, sensing electrographic signals from the cardiac tissue.

There is further provided, in accordance with some embodiments of the present invention, a method that includes drilling multiple narrower channels, and one or more wider channels, through a flexible electrically-insulating substrate, such that the narrower channels and the wider channels pass between an inner surface of the substrate and an outer surface of the substrate. The method further includes, using an electrically-conducting metal, at least partly covering the inner surface and the outer surface, completely filling the narrower channels, and plating the wider channels.

In some embodiments, at least partly covering the inner surface and the outer surface, completely filling the narrower channels, and plating the wider channels includes at least partly covering the inner surface and the outer surface, completely filling the narrower channels, and plating the wider channels by:
 depositing the electrically-conducting metal onto the inner surface and the outer surface of the substrate, and into the narrower channels and the wider channels;
 subsequently to depositing the electrically-conducting metal onto the inner surface of the substrate, while the outer surface of the substrate is covered, plating the substrate in a plating bath of the electrically-conducting metal for a first time interval;
 subsequently to plating the substrate for the first time interval, at least partly uncovering the outer surface of the substrate; and
 subsequently to at least partly uncovering the outer surface of the substrate, plating the substrate in the plating bath for a second time interval.

In some embodiments, the method further includes:
 bonding the electrically-conducting metal that covers the inner surface to a supporting structure; and
 shaping the substrate and the supporting structure to define an interior lumen.

In some embodiments, shaping the substrate and the supporting structure includes shaping the substrate and the supporting structure to define a thimble that contains the interior lumen.

In some embodiments, the method further includes etching one or more electrically-conductive traces onto the inner surface of the substrate,
 depositing the electrically-conducting metal onto the inner surface of the substrate includes depositing the electrically-conducting metal onto the inner surface of the substrate such that the electrically-conductive traces remain electrically isolated from the electrically-conducting metal,
 the method further includes forming holes in the substrate opposite the traces, respectively, and
 depositing the electrically-conducting metal onto the outer surface of the substrate includes depositing the electrically-conducting metal onto the outer surface of the substrate such as to form (i) a main portion, and (ii) one or more islands that are electrically isolated from the main portion and contact the traces, respectively, by virtue of at least partly filling the holes.

The present invention will be more fully understood from the following detailed description of embodiments thereof, taken together with the drawings, in which:

BRIEF DESCRIPTION OF THE DRAWINGS

FIG. 3 schematically illustrates a longitudinal cross-section through the distal tip shown in FIG. 2A, in accordance with some embodiments of the present invention;

DETAILED DESCRIPTION OF EMBODIMENTS

Overview

Figure 1:
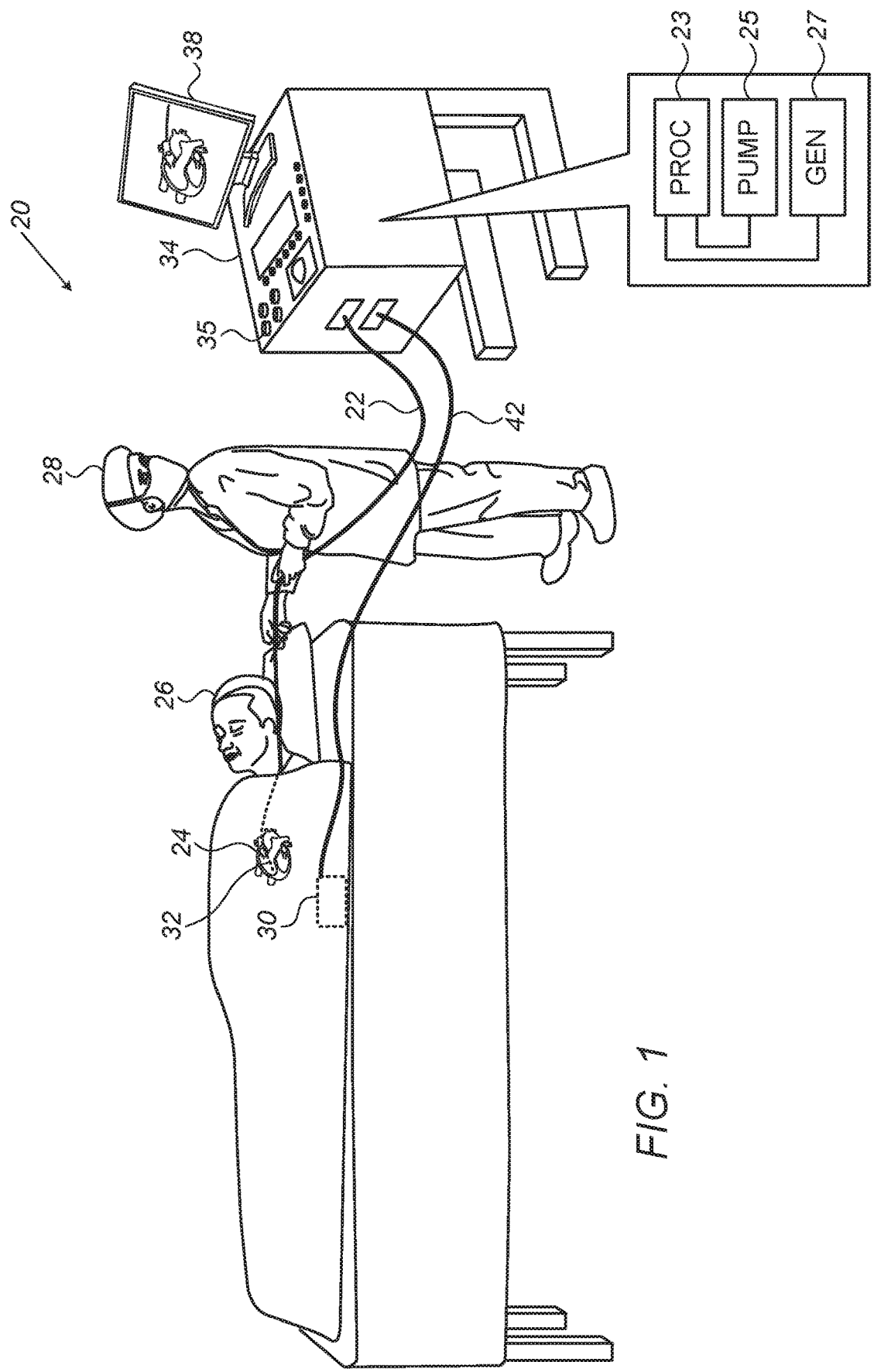
FIG. 1 is a schematic illustration of a system for ablating tissue of a subject, in accordance with some embodiments of the present invention.

Embodiments of the present invention include an ablation electrode comprising at least one flexible printed circuit board (PCB) that is bonded, by an adhesive, to a supporting metallic sheet. The flexible PCB comprises a flexible electrically-insulating substrate comprising an outer surface that is coated by an outer layer of an electrically-conducting (and biocompatible) metal, such as gold, palladium, or platinum, and an inner surface that is coated by an inner layer of the same (and/or another) electrically-conducting metal. The inner surface may further support one or more electric components such as sensors (e.g., thermocouples) and traces, which are electrically isolated from the inner metallic layer. Following the deposition of the electric components, the coating of the substrate, and the bonding of the PCB to the supporting sheet, the flexible PCB (together with the supporting sheet) may be deformed into any suitable shape. For example, in some embodiments, the flexible PCB is deformed into a thimble-shaped electrode, referred to hereinbelow as a "tip electrode." The electrode is then coupled to the distal end of a catheter.

During an ablation procedure, the outer metallic layer is brought into contact with the tissue that is to be ablated, and ablating currents are then passed, via the outer metallic layer, into the tissue. While the ablating currents are applied to the tissue, the sensors may acquire any relevant physiological readings from the tissue. Typically, open, plated vias, which pass through the electrode, provide electrical connectivity between the inner and outer metallic layers, such that the ablating currents may pass outward through the plated vias, and electrographic signals from the tissue may pass inward through the plated vias. Electrical connectivity may also be provided by blind vias, each such via being formed by the removal of a portion of the substrate such that the outer metallic layer directly contacts a trace underneath.

The aforementioned plated vias also provide fluid communication between the inner and outer surfaces of the electrode, such that an irrigating fluid (e.g., saline) may pass through the plated vias into the surrounding blood. The irrigating fluid evacuates heat from the interior of the electrode into the blood, and additionally dilutes the blood at the tissue-electrode interface, thus reducing the probability of coagulum or charring. Due to the fact that the plated vias provide for passage of the irrigating fluid therethrough, the plated vias may also be referred to as "irrigation channels" or "irrigation holes."

A challenge, when using the type of electrode described above, is that the substrate may provide significant thermal resistance, such as to limit the amount of heat that is transferred from the tissue-electrode interface to the interior of the electrode. This, in turn, limits the amount of heat that may be evacuated by the irrigating fluid.

To address this challenge, embodiments described herein provide a large number (e.g., tens of thousands) of small, closed vias, referred to hereinbelow as "thermal vias," that increase the thermal connectivity between the two surfaces of the electrode. Such thermal vias may comprise, for example, columns of an electrically-conducting metal, such as gold, that connect the outer metallic layer to the inner metallic layer. Typically, the thermal vias are distributed over the entire surface of the electrode. The thermal vias increase the amount of heat that is transferred to the interior of the electrode, thus facilitating the evacuation of heat by the irrigating fluid.

Embodiments of the present invention also include a manufacturing process for the electrode. Typically, both surfaces of the substrate are initially coated with copper; hence, the manufacture of the electrode typically begins with the etching away of this copper, except for where copper traces are required on the inner surface of the substrate. Next, constantan traces, to be used for thermocouples, are deposited onto the inner surface. Subsequently, one or more wide channels, a large number of relatively narrow channels, and, optionally, one or more blind vias, are drilled through the substrate.

Subsequently, on the inner surface of the substrate, a mask is applied over the traces and the surrounding exclusion zones that will insulate the traces from the inner metallic layer. (The mask is not applied over the portions of the constantan traces that are designated as thermocouple junctions.) Similarly, on the outer surface, another mask is applied over exclusion zones that will insulate microelectrode "islands" from the rest of the outer metallic layer.

Next, a thin layer of metal (typically gold) is sputtered into the channels and onto both surfaces of the substrate. The metal sputtered onto the inner surface includes traces that intersect the constantan traces, thus forming thermocouple junctions. Following the sputtering of the metal, the masks are removed, the interior traces and exclusion zones are covered by another mask, and the entire outer surface is also masked.

Subsequently, the substrate is placed in a plating bath for a period of time, such that (i) any remaining exposed portions of the inner surface of the substrate are covered by the metal, i.e., the layer of metal expands laterally over the inner surface, (ii) the thickness of the inner layer is increased, (iii) the narrow channels are sealed shut, thus becoming thermal vias, and (iv) the wide channels are narrowed, thus becoming plated irrigation channels. The interior and exterior surfaces are then unmasked. Next, the interior traces and exclusion zones are covered by at least one coverlay.

Subsequently, the substrate is returned to the plating bath for another period of time, such that the thickness of both the outer layer and inner layer are increased, and the plated irrigation channels are narrowed. Typically, the total duration of time for which the substrate remains in the plating bath is set such that the thickness of the inner layer reaches the thickness of the coverlay. (Typically, the thickness of the outer layer is not increased significantly, so as to reduce the risk of the outer layer cracking when the substrate is folded into its final shape.)

Next, apertures, which have a diameter greater or equal to that that of the irrigation holes, are drilled through a supporting sheet of metal, comprising, for example, an alloy of cobalt chromium. The supporting sheet is then bonded to the inner metallic layer and the coverlay, such that the apertures in the supporting sheet are aligned with the irrigation channels in the substrate. Subsequently, the plated substrate and supporting sheet are deformed into their desired shape. Finally, the relevant wires are connected to the electrode, and the electrode is then coupled to the catheter.

System Description

Reference is initially made to FIG. 1, which is a schematic illustration of a system 20 for ablating tissue of a subject 26, in accordance with some embodiments of the present invention.

FIG. 1 depicts a physician 28 performing a unipolar ablation procedure on subject 26, using an ablation catheter 22. In this procedure, physician 28 first inserts the distal tip 32 of catheter 22 into the subject, and then navigates distal tip 32 to the tissue that is to be ablated. For example, the physician may advance the distal tip through the vasculature of the subject until the distal tip is in contact with cardiac tissue belonging to the heart 24 of the subject. Next, while distal tip 32 contacts the tissue, the physician causes radiofrequency (RF) electric currents to be passed between distal tip 32 and a neutral electrode patch 30 that is coupled externally to the subject, e.g., to the subject's back.

To facilitate navigating the catheter, catheter 22 may comprise one or more electromagnetic position sensors, which, in the presence of an external magnetic field, generate signals that vary with the positions of the sensors. Alternatively or additionally, any other suitable tracking system, such as an impedance-based tracking system, may be used. For example, both electromagnetic tracking and impedance-based tracking may be used, as described, for example, in U.S. Pat. No. 8,456,182, whose disclosure is incorporated herein by reference.

Catheter 22 is proximally connected to a console 34, comprising, for example, a processor (PROC) 23, a pump 25, and a signal generator (GEN) 27. (Electrode patch 30 is typically also connected to console 34, via a wire 42.) During the ablation procedure, signal generator 27 generates the aforementioned ablating currents. These currents are carried through catheter 22, over one or more wires, to distal tip 32. Additionally, pump 25 supplies an irrigating fluid, such as saline, to the distal tip of the catheter, as further described below with reference to FIGS. 2A-B and FIG. 3.

Console 34 further comprises controls 35, which may be used by the physician to control the parameters of the ablating currents. In particular, in response to the manipulation of controls 35 by physician 28, processor 23 may adjust the parameters of the ablating currents, by outputting appropriate instructions to signal generator 27 over any suitable wired or wireless communication interface. Processor 23 may similarly control pump 25 over any suitable wired or wireless interface. In addition, the processor may receive and process any relevant signals from the distal tip of the catheter, such as the signals received from any of the sensors described herein.

In some embodiments, system 20 further comprises a display 38, which may display relevant output to physician 28 during the procedure.

Notwithstanding the particular type of procedure depicted in FIG. 1, it is noted that the embodiments described herein may be applied to any suitable type of ablation procedure, or any other procedure that necessitates the transfer of heat through a flexible PCB.

The Distal Tip of the Catheter

Figure 2A:
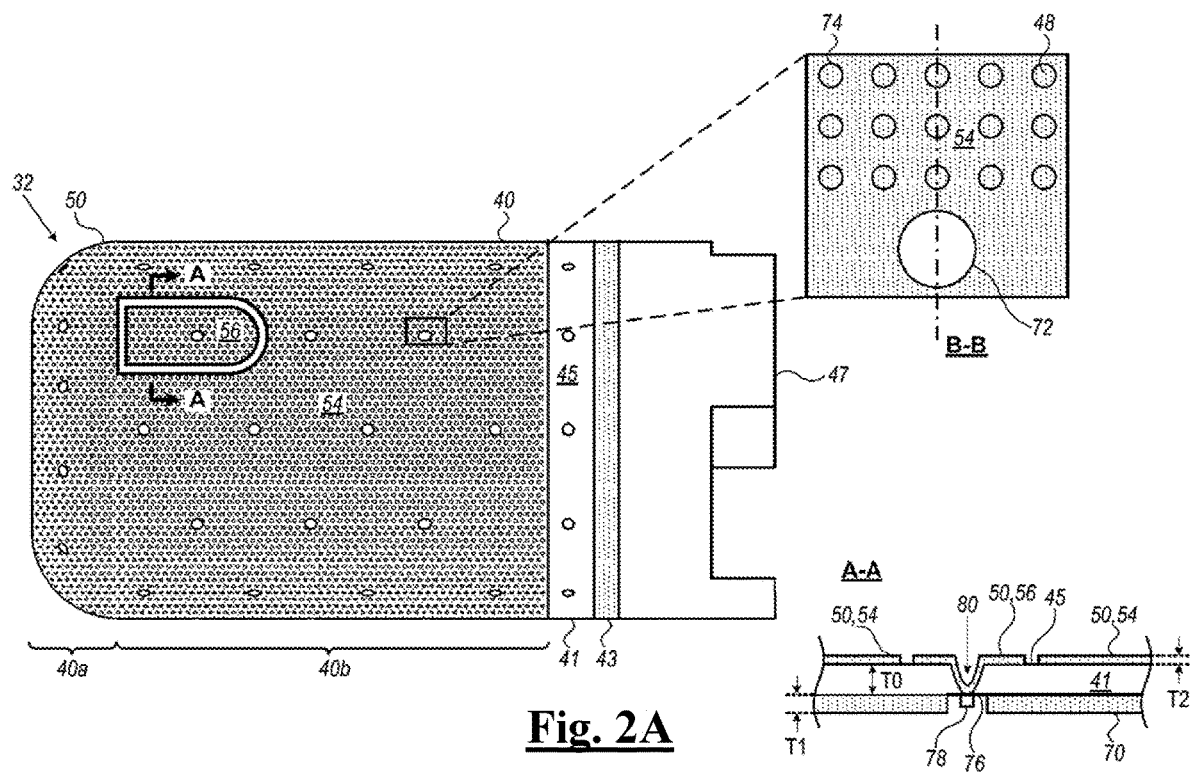
FIG. 2A is a schematic illustration of a distal tip of a catheter, in accordance with some embodiments of the present invention.

Reference is now made to FIG. 2A, which is a schematic illustration of distal tip 32, in accordance with some embodiments of the present invention. Reference is additionally made to FIG. 3, which schematically illustrates a longitudinal cross-section through distal tip 32, in accordance with some embodiments of the present invention.

Distal tip 32 comprises at least one ablation electrode 40, such as the tip electrode depicted in FIG. 2A and FIG. 3. Electrode 40 comprises a plated flexible electrically-insulating substrate 41 that is bonded, by an adhesive, to a supporting structure 36 at the distal end of catheter 22. Substrate 41 may be made of any suitable flexible electrically-insulating material, such as a flexible polymer (e.g., polyimide) or liquid crystal polymer (LCP). Supporting structure 36 may be made of any suitably strong material, such as cobalt chromium, stainless steel, magnesium, and/or an alloy of any of the above. For example, supporting structure 36 may comprise the L-605 cobalt-chromium-tungsten-nickel alloy.

In general, electrode 40 may have any suitable shape. In some embodiments, as shown in FIG. 2A and FIG. 3, electrode 40 is thimble-shaped, comprising a cylindrical portion 40b that is capped by a dome-shaped portion 40a. Typically, tabs 47 at the proximal end of the electrode comprise soldering pads onto which wires, which run through the length of the catheter, may be soldered, such as to establish electrical connectivity between the electrode and the proximal end of the catheter. These soldering pads are described in further detail below, with reference to FIGS. 4-5.

As shown in the "A-A" cross-section of FIG. 2A, substrate 41 comprises an inner surface 76, which faces supporting structure 36, and an outer surface 45, which faces away from supporting structure 36. Typically, the thickness T0 of the substrate—i.e., the distance between the inner and outer surfaces of the substrate—is between 5 and 75 (e.g., between 12 and 50) microns. At least part of the inner surface is covered by an inner layer 70 of an electrically-conducting metal, such as gold. Typically, inner layer 70 has a thickness T1 of between 10 and 50 microns. Similarly, at least part of outer surface 45 is covered by an outer layer 50 of the metal. Typically, outer layer 50 has a thickness T2 of between 1 and 5 microns.

Typically, outer layer 50 is discontinuous, in that the outer layer comprises a main portion 54 along with one or more isolated portions that are electrically isolated from main portion 54 by exposed portions of the substrate. These isolated portions may include one or more "islands" that function as sensing microelectrodes 56. For example, outer layer 50 may comprise 3-7 microelectrodes 56 distributed around the circumference of the distal tip. Alternatively or additionally, the isolated portions may comprise a sensing ring electrode 43, which may be disposed, for example, near the proximal end of distal tip 32.

A respective electrically-conductive trace 78, which is electrically isolated from inner layer 70 by an exposed portion of inner surface 76, is disposed beneath each of the sensing electrodes. As further described below with reference to FIG. 4, prior to forming the sensing electrodes, holes, referred to herein as blind vias 80, are formed (e.g., drilled) in the substrate above traces 78. Subsequently, as the sensing electrodes are deposited onto the outer surface of the substrate, the sensing electrodes at least partly fill blind vias 80, thus contacting the traces. Hence, during the procedure, electrographic signals from the cardiac tissue of the subject that are sensed by the sensing electrodes may be carried over traces 78 to wires that run through catheter 22 to the proximal end of the catheter. The signals may thus be delivered to processor 23 for analysis.

Figure 2B:
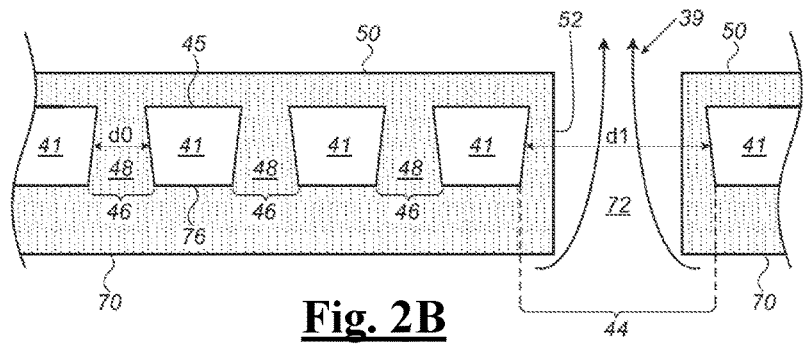
FIG. 2B schematically illustrates a cross-section through a portion of a tip electrode, in accordance with some embodiments of the present invention.

Reference is now additionally made to FIG. 2B, which schematically illustrates a cross-section through a portion of electrode 40, in accordance with some embodiments of the present invention. FIG. 2B corresponds to the "B-B" cross-section indicated in FIG. 2A.

Substrate 41 is shaped to define a plurality of channels, including multiple narrower channels 46 and one or more wider channels 44, that pass between the inner and outer surfaces of the substrate. Typically, each channel is tapered along the length of the channel, with the cross-sectional area of the channel at the inner surface of the substrate being slightly greater than the cross-sectional area at the outer surface. The cross-sectional area (or average cross-sectional area) of each narrower channel 46 is less than that of each wider channel 44.

In some embodiments, the channels have a circular cross-section. In such embodiments, the average diameter d0 of each of the narrower channels may be less than 50% (e.g., less than 25%) of the average diameter d1 of each of the wider channels. Alternatively or additionally, diameter d0 may be between 5 and 50 (e.g., between 5 and 30) microns, and/or diameter d1 may be between 50 and 300 microns. In other embodiments, at least some of the channels may have a cross-section having a square shape, or any other suitable shape. (In such embodiments, the average cross-sectional area of each of the channels may correspond to that implied above by the ranges for d0 and d1.)

Typically, the electrode includes 30-100 wider channels. Each wider channel 44 is plated by a plating layer 52 of the electrically-conducting metal, which connects outer layer 50 to inner layer 70. The plated wider channels thus provide electrical and thermal conductivity between the outer and inner layers of metal. Moreover, the plated wider channels provide a fluid passageway between the interior and exterior of distal tip 32, such that an irrigating fluid 39, supplied by pump 25 (FIG. 1), may flow therethrough. Hence, the plated wider channels may be referred to as "irrigation holes" 72. (The diameter of each irrigation hole is smaller than diameter d1 by approximately twice the thickness of plating layer 52.) Supporting structure 36 is shaped to define apertures 62 that are aligned with irrigation holes 72, such that the supporting structure does not obstruct the irrigation holes.

Typically, the number of narrower channels 46 is relatively large. For example, substrate 41 may be shaped to define at least 1,000, 5,000, 10,000, or 20,000 narrower channels. Alternatively or additionally, the ratio of narrower channels to wider channels may be at least 300:1. Alternatively or additionally, the total area of the respective outer openings of the narrower channels (i.e., the openings of the narrower channels at the outer surface of the substrate) may be at least 10%, 20%, or 30% of the area of the outer surface of the substrate. Thus, for example, if the area of the outer surface of the substrate (including the narrower channels) is 27 mm$^2$, and each of the narrower channels includes a circular outer opening having a diameter of 25 microns (and hence an area of 0.0005 mm$^2$), the number of narrower channels may be approximately 16,500 (for a total area of 8.1 mm$^2$), such that the outer openings of the narrower channels cover approximately 30% of the outer surface.

In contrast to the wider channels, narrower channels 46 are not merely plated, but rather, are filled by respective columns 48 of the electrically-conducting metal, which connect outer layer 50 to inner layer 70. (Columns 48 are not necessarily cylindrical, since, as noted above, narrower channels 46 do not necessarily have a circular cross-section. Furthermore, as noted above, the cross-sectional area of each column may vary along the length of the column. It is noted that outer layer 50, inner layer 70, plating layer 52 and columns 48 may be collectively described as a single body of metal that covers the substrate.) Due to the large number of channels 46, and by virtue of each of these channels being filled, a large amount of heat may be transferred via channels 46. Hence, the filled narrower channels may be referred to as "thermal vias" 74. (For ease of illustration, no thermal vias are shown in the "A-A" cross section of FIG. 2A.)

Notwithstanding the above, it is noted that in some embodiments, the narrower channels are not filled, but rather, are merely plated, similarly to the wider channels. Even in such embodiments, a large amount of heat may be transferred to the interior of the electrode.

Typically, catheter 22 comprises a fluid-delivery tube (not shown), which runs through the full length of the tubular body 22m of catheter 22. The fluid-delivery tube is distally coupled to a flow diverter 60 that is shaped to define one or more fluid-flow apertures 64. Flow diverter 60 diverts fluid 39, which is received, via the fluid-delivery tube, from the proximal end of the catheter, through fluid-flow apertures 64. In such embodiments, electrode 40 may be coupled to the base 58 of flow diverter 60, such that the flow diverter is disposed inside of the interior lumen of the electrode. For example, supporting structure 36 may be bonded to base 58. Alternatively or additionally, base 58 may be shaped to define a plurality of protrusions, and supporting structure 36 may be shaped to define a plurality of complementary holes, such that the protrusions snap into the holes.

As described above with reference to FIG. 1, during the ablation procedure, physician 28 contacts tissue of subject 26 with distal tip 32, and in particular, with outer layer 50. While contacting the tissue with outer layer 50, the physician passes electric currents, via the outer layer, into the tissue. The electric currents cause heat to be generated in the tissue, such that a lesion is formed in the tissue. This heat is transferred, via thermal vias 74 (i.e., via columns 48) to inner layer 70. At the same time, pump 25 (FIG. 1) pumps irrigating fluid 39 through the fluid-delivery tube, such that the fluid flows into the interior of the electrode through fluid-flow apertures 64 of flow diverter 60. This fluid then flows out of the distal tip through apertures 62 and irrigation holes 72, thus evacuating the heat from inner layer 70 into the subject's blood.

Manufacturing the Distal Tip

Figure 4:
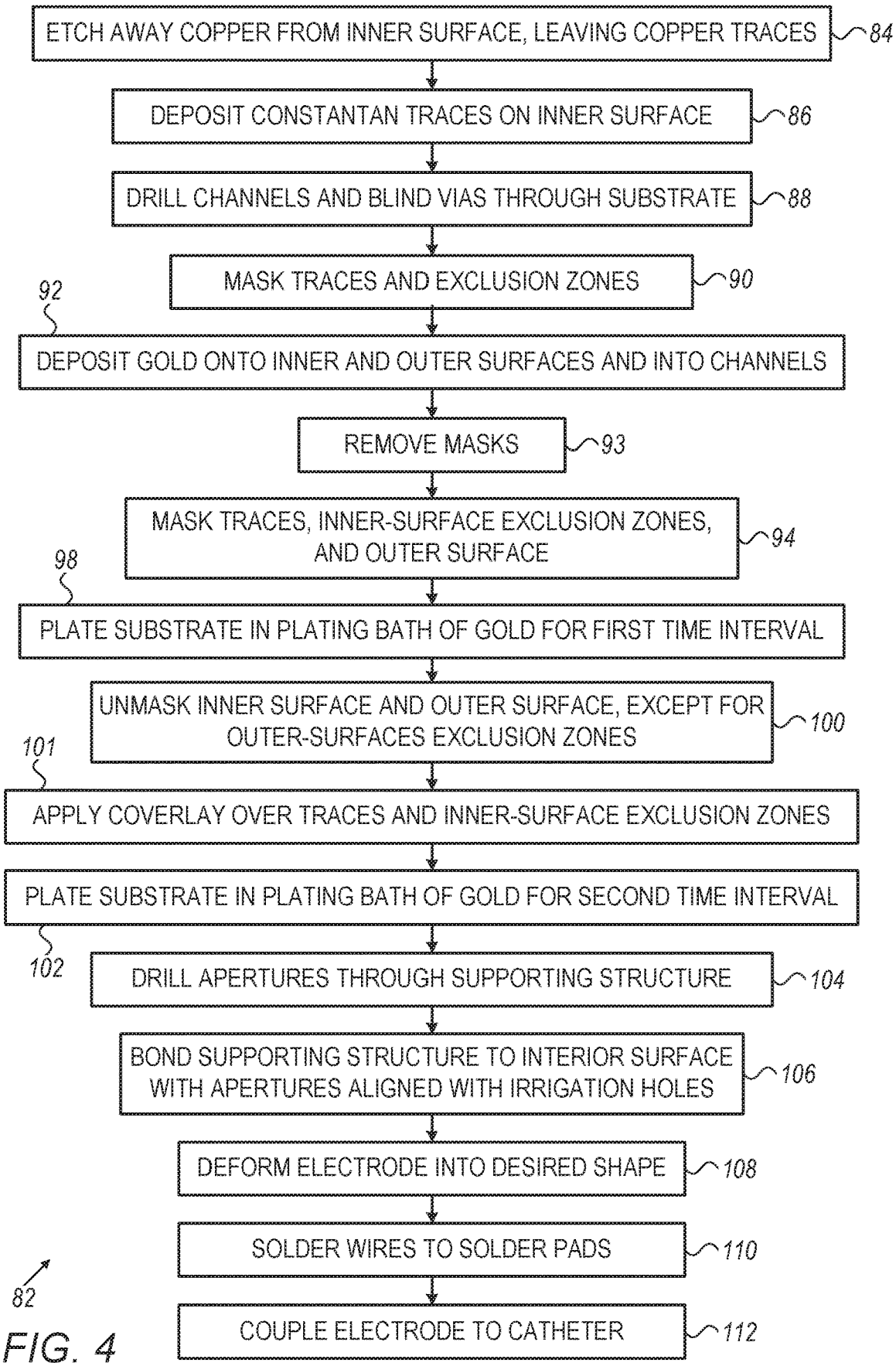
FIG. 4 is a flow diagram for a method of manufacturing a tip electrode, in accordance with some embodiments of the present invention.
Figure 5:
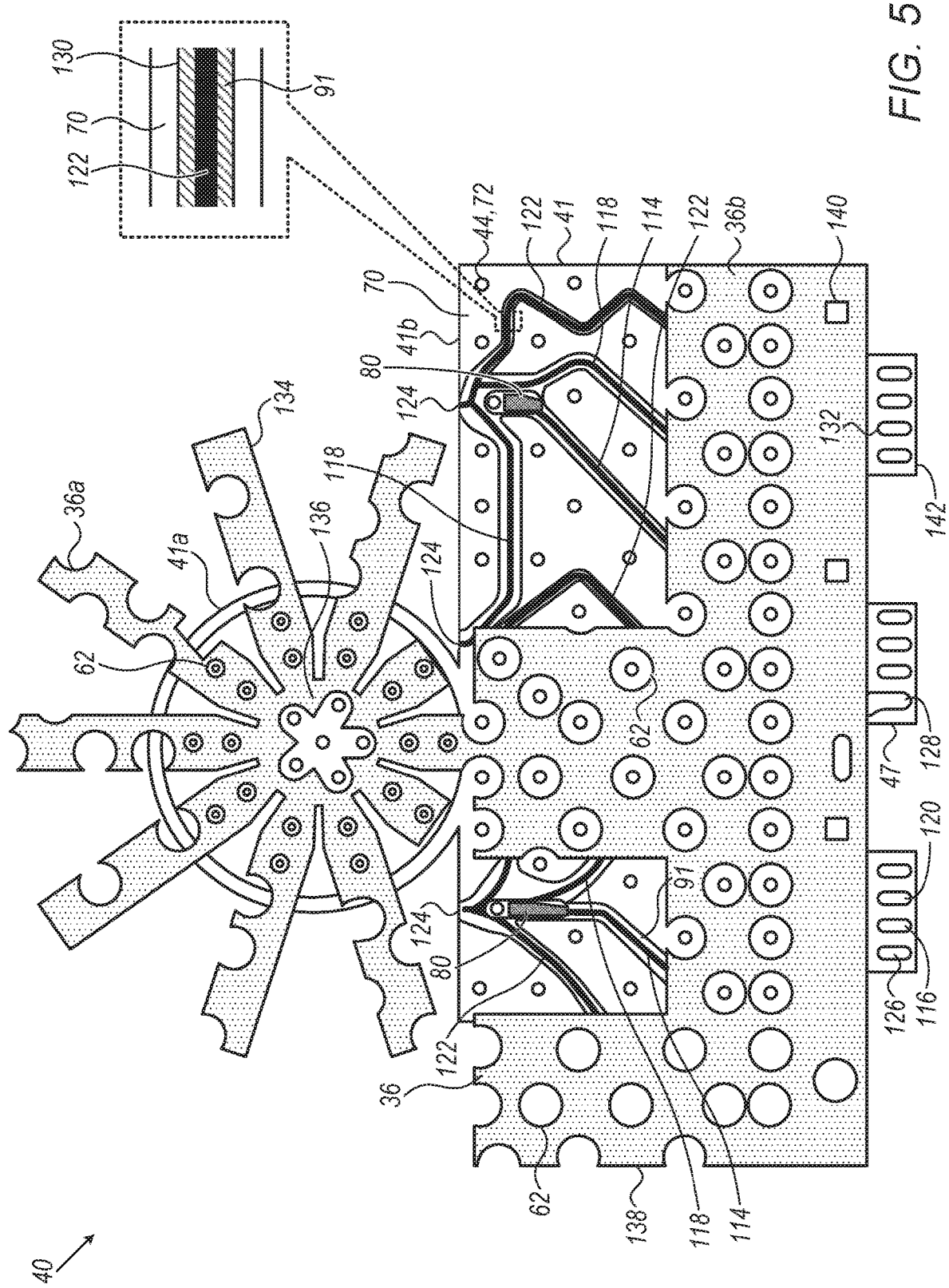
FIG. 5 is a schematic illustration of a tip electrode prior to the deformation thereof, in accordance with some embodiments of the present invention.

Reference is now made to FIG. 4, which is a flow diagram for a method 82 of manufacturing electrode 40, in accordance with some embodiments of the present invention. Reference is additionally made to FIG. 5, which is a schematic illustration of electrode 40 prior to the deformation thereof, in accordance with some embodiments of the present invention. (FIG. 5 shows the interior of electrode 40, i.e., the various elements that are coupled to the inner surface of substrate 41.)

FIG. 4 assumes that at least the inner surface of the substrate is initially coated with a layer of copper. Hence, method 82 begins with an etching step 84, in which all of the copper is etched away from the inner surface, with the exception of copper traces 114, which are to be connected to the sensing electrodes on the exterior of the electrode. (Any copper on the outer surface is also etched away.) This etching may be performed, for example, by placing a mask over the portions of the copper that are designated for traces 114, and then chemically removing the exposed copper. Alternatively, if the inner surface of the substrate is initially exposed, copper traces 114 may be deposited onto the inner surface.

Subsequently, at a trace-depositing step 86, constantan traces 118, which are to be used for thermocouples, are deposited onto the inner surface of the substrate. Trace-depositing step 86 may be performed, for example, by physical vapor deposition (PVD), such as sputter deposition. For example, a mask may be placed over the entire inner surface, with the exception of those portions of the inner surface that are designated for constantan traces 118. Subsequently, a seed layer of a base metal, such as titanium-tungsten, may be sputtered onto the substrate. Finally, the constantan may be sputtered over the base metal.

Typically, to minimize the required wiring, the constantan traces terminate at a common constantan-trace soldering pad 120. In some embodiments, prior to the deposition of the constantan, a hole (or "stake via") is drilled through the substrate at the site of soldering pad 120. Subsequently, the deposited constantan fills the hole, and then forms soldering pad 120 above the hole. Alternatively, instead of drilling completely through the substrate, a depression may be drilled into the substrate, such that the deposited constantan fills the depression. In either case, soldering pad 120 is "staked" to the substrate by the constantan underneath the soldering pad. (To facilitate the filling of the hole or depression, a draft angle may be used to taper the hole or depression, as described immediately below for the narrower and wider channels.)

Next, at a drilling step 88, multiple narrower channels and one or more wider channels 44 are drilled through the substrate, typically using laser drilling. (The wider channels, but not the narrower channels, may be seen in FIG. 5.) Typically, the channels are drilled from the inner surface of the substrate, using a draft angle such that the channels narrow as they approach the outer surface; this facilitates the collection of metal onto the walls of the channels during the subsequent sputtering process. In addition, blind vias 80 may be drilled (e.g., laser-drilled) through the substrate from the outer surface of the substrate at those portions of the outer surface that are designated for sensing electrodes, using copper traces 114 as stops. (In other words, portions of the substrate that are disposed over the copper traces may be removed, thus exposing the copper traces.) Typically, a draft angle is used for the blind vias, such that the blind vias narrow as they approach the inner surface of the substrate; this facilitates the collection of metal onto the walls of the blind vias.

Next, at a first masking step 90, the copper and constantan traces, along with exclusion zones 91 (i.e., exposed portions of the inner surface of the substrate) that are designated for insulating these traces, are masked. (Portions of the constantan traces that are designated for the thermocouple junctions are not masked.) Additional exclusion zones designated for insulating the gold traces that will intersect the constantan traces (thus forming constantan-gold thermocouples) are also masked. Additionally, exclusion zones on the outer surface that are designated for insulating the sensing electrodes are masked.

Subsequently, at a depositing step 92, a thin layer of gold is deposited onto the inner and outer surfaces of the substrate and into the channels. Depositing step 92 may be performed, for example, by physical vapor deposition (PVD), such as sputter deposition. (Typically, a seed layer of a base metal, such as titanium-tungsten, is sputtered onto the substrate prior to the sputtering of the gold.) By virtue of the masks, the gold is not deposited onto the traces or exclusion zones.

The deposited gold includes an initializing layer for inner layer 70, outer layer 50, plating layer 52, and columns 48. The deposited gold further includes gold traces 122 that cover the constantan traces at thermocouple junctions 124. Each gold trace 122 terminates at a respective gold-trace soldering pad 126. The deposited gold further includes a respective copper-trace soldering pad 116 for each of the copper traces. In some embodiments, copper-trace soldering pads 116 and/or gold-trace soldering pads 126 are staked to the substrate, as described above for the constantan-trace soldering pad. The deposited gold further includes at least one gold soldering pad 128, which is connected to inner layer 70. Gold soldering pad 128 may also be staked to the substrate.

Following the deposition, the masks (along with any gold that was deposited onto the masks) are removed at a mask-removing step 93. Subsequently, at a second masking step 94, the traces, the inner-surface exclusion zones that surround the traces, and the entire outer surface of the substrate are masked.

Following second masking step 94, while the traces and outer surface remain masked, the substrate is plated in a plating bath of gold for a first time interval, at a first plating step 98. The plating of the substrate causes any gaps in the gold to be filled, and further increases the thickness of the gold, such that, for example, inner layer 70 reaches a thickness of between 5 and 40 microns, while the diameter of the wider channels is reduced to between 30 and 200 microns. Additionally, the narrower channels may become completely filled.

Typically, the plating of the substrate is electrochemical, whereby the flow of electric current through the gold that already coats the substrate causes this gold to attract gold ions in the plating bath. The amplitude and duration of the current may be controlled such that the gold reaches the desired thickness.

Following first plating step 98, the inner and outer surfaces of the substrate, with the exception of the aforementioned exclusion zones designated to insulate the sensing electrodes, are unmasked, at an unmasking step 100. Next, at a coverlay-applying step 101, at least one coverlay 130 is applied over the traces and inner-surface exclusion zones. (In some embodiments, as illustrated in the inset portion of FIG. 5, coverlay 130 is transparent or nearly transparent.)

Typically, the proximal portion of coverlay 130 that covers tabs 47 is shaped to define windows 132 that expose the soldering pads, such that the soldering pads may be thickened during the subsequent plating process. (An additional cover 142, having windows that are aligned with windows 132, may cover the proximal portion of the coverlay.) Typically, the soldering pads are not completely exposed, but rather, are held "captive" by coverlay 130, in that one or more edges of each soldering pad are covered by the rims of windows 132. Coverlay 130 thus helps hold the soldering pads to substrate 41 during the subsequent soldering process.

Subsequently, at a second plating step 102, the substrate is plated in the plating bath for a second time interval, such that any gaps in outer layer 50 are filled, while the inner, outer, and plating layers are thickened. For example, the second plating may increase the thickness of the inner layer to between 10 and 50 microns, while reducing the diameter of the wider channels to between 15 and 150 microns. Typically, the final thickness of the inner layer is the same as the thickness of the coverlay, such as to attain a smooth interior surface. (To avoid any confusion, the term "interior surface" is used herein to refer to the surface that is formed by the coverlay and the inner gold layer, whereas the term "inner surface" is used to refer to the underlying surface of the substrate.) Additionally, in the event that the narrower channels were not completely filled during first plating step 98, these channels are completely filled during second plating step 102. As in the case of first plating step 98, the amplitude and duration of the electric current in the plating bath may be controlled such that the desired thicknesses are attained.

(In some embodiments, the outer surface is masked prior to depositing step 92, such that no gold is deposited onto the outer surface during depositing step 92. In such embodiments, following unmasking step 100 and prior to second plating step 102, a thin layer of gold is deposited onto the outer surface.)

Subsequently to second plating step 102, at an aperture-drilling step 104, apertures 62 are drilled through supporting structure 36. (Alternatively to drilling, any other suitable technique, such as chemical etching, may be used to form the apertures.) Next, at a bonding step 106, by the application of a suitable adhesive between supporting structure 36 and the smooth interior surface that is formed by coverlay 130 and inner layer 70, the supporting structure is bonded to the interior surface, with apertures 62 being aligned with irrigation holes 72. Typically, the area of the apertures is greater than that of the irrigation holes, such as to compensate for any small misalignments when bonding the supporting structure.

Next, at a deforming step 108, electrode 40 is deformed into the desired shape. For example, the electrode may be inserted into a forming jig that shapes the electrode around a suitable mandrel. Following the insertion of the electrode into the jig, the jig is placed inside an oven. Subsequently, the oven heats the electrode to a suitable temperature, while pressure is applied to the electrode. The combination of heat and pressure causes the electrode to bond to itself in the desired shape.

In general, the substrate and supporting structure may be deformed into any desired shape. Typically, however, during deforming step 108, the substrate and supporting structure are shaped to define an interior lumen; for example, the substrate and supporting structure may be shaped to define a thimble that contains an interior lumen, as described above with reference to FIG. 2A and FIG. 3. Alternatively, for example, the substrate and supporting structure may be shaped to define a ring.

Typically, to facilitate the manufacture of a thimble-shaped electrode, substrate 41 comprises two portions that are continuous with one another: a distal, circular portion 41a, and a proximal, rectangular portion 41b. Similarly, supporting structure 36 comprises two portions that are continuous with one another: a distal supporting portion 36a, typically comprising a plurality of spokes 134 that radiate from a central hub 136, and a proximal supporting portion 36b. During bonding step 106, distal supporting portion 36a is bonded to the interior surface of circular portion 41a, and the adhesive is applied to the outer surfaces of spokes 134. (These surfaces are opposite the surfaces shown in FIG. 5.) In addition, proximal supporting portion 36b is bonded to the interior surface of rectangular portion 41b, leaving some distal portions of this interior surface exposed. The adhesive is applied to the outer surface of an overhanging tab 138 of proximal supporting portion 36b, which hangs over the side of rectangular portion 41b. (Proximal supporting portion 36b may also hang over the proximal end of rectangular portion 41b.)

Subsequently, during deforming step 108, distal supporting portion 36a and circular portion 41a are folded over the top of the mandrel, while proximal supporting portion 36b and rectangular portion 41b are rolled around the mandrel. To maintain this configuration, the outer surfaces of spokes 134 are bonded to the exposed distal portions of the interior surface of rectangular portion 41b, and the outer surface of tab 138 is bonded to the opposite end of proximal supporting portion 36b. (Additionally, the inner surface of at least one of the spokes may bond to tab 138.) Thus, distal supporting portion 36a and circular portion 41a are formed into dome-shaped portion 40a (FIG. 2A), while proximal supporting portion 36b and rectangular portion 41b are formed into cylindrical portion 40b.

Subsequently, at a soldering step 110, wires are soldered onto the soldering pads. In particular, the wire that delivers RF currents from generator 27 (FIG. 1) is soldered onto gold soldering pad 128, while other wires, which deliver signals to processor 23, are soldered to the other soldering pads.

Finally, at a coupling step 112, the electrode is coupled to the catheter. For example, proximal supporting portion 36b may be bonded to base 58 of the flow diverter (FIG. 3). Alternatively or additionally, as described above with reference to FIG. 3, protrusions belonging to base 58 may snap into complementary holes 140 in proximal supporting portion 36b. Subsequently, the flow diverter may be coupled to the fluid-delivery tube belonging to the catheter. (Alternatively, the flow diverter may be coupled to the fluid-delivery tube before the electrode is coupled to the flow diverter.)

In general, any suitable masking technique may be used at each of the steps in which a mask is required. Examples of suitable masks include liquid and film photoresists.

Alternatively or additionally to the traces described above, any other suitable electric or electronic components may be deposited onto the inner surface of the substrate. Such components may include thermistors for measuring the temperature of the tissue, pressure sensors for measuring the pressure applied to the distal end of the catheter, and/or electromagnetic sensors for navigating the catheter. These components (along with suitable surrounding exclusion zones) may be masked or covered whenever such masking or covering is required, as described above for the traces.

It is noted that the scope of the present disclosure includes any suitable modification to method 82 with respect to the order of the steps that are performed and/or with respect to the various materials that are used, as will be apparent to any person of skill in the art. For example, any suitable electrically-conducting metal may be used in lieu of copper, gold, or constantan.

In general, the embodiments described herein may be combined with any of the embodiments described in US Patent Application Publication 2018/0110562 or U.S. patent application Ser. No. 15/793,126, whose respective disclosures are incorporated herein by reference.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An ablation electrode for a catheter, the ablation electrode comprising:
    a supporting structure comprising a dome shaped distal portion at a catheter tip; and
    a flexible electrically-insulating substrate comprising an inner surface and an outer surface in which an outer layer of an electrically-conducting metal covers at least part of the outer surface and an inner layer of the electrically-conducting metal covers at least part of the inner surface and is bonded to the dome shaped distal portion of the supporting structure, the flexible electrically-insulating substrate being shaped to define:
    (i) multiple narrower channels passing between the inner surface and the outer surface with respective columns of the electrically-conducting metal that fill the multiple narrower channels so as to connect the outer layer to the inner layer, and
    (ii) one or more wider channels passing between the inner surface and the outer surface with a layer of the electrically-conductive metal that plates the wider channels to connect the outer layer to the inner layer to provide for a fluid passageway for passage of irrigation fluid therethrough.

2. The ablation electrode according to claim 1, wherein the flexible electrically-insulating substrate is shaped to define at least 1,000 of the multiple narrower channels.

3. The ablation electrode according to claim 1, wherein the total area of respective outer openings of the multiple narrower channels is at least 10% of an area of the outer surface.

4. The ablation electrode according to claim 1, wherein the electrically-conducting metal comprises gold.

5. The ablation electrode according to claim 4, further comprising:
    at least one constantan trace disposed on the inner surface and electrically isolated from the inner layer; and
    at least one gold trace disposed on the inner surface, electrically isolated from the inner layer, and covering the constantan trace at a thermocouple junction.

6. The ablation electrode according to claim 1, wherein the flexible electrically-insulating substrate and the supporting structure are shaped to define an interior lumen.

7. The ablation electrode according to claim 6, wherein the flexible electrically-insulating substrate and the supporting structure are shaped to define a thimble that contains the interior lumen.

8. The ablation electrode according to claim 6, wherein the catheter tip comprises a flow diverter configured to divert fluid received from a proximal end of the catheter, and wherein the supporting structure is coupled to the flow diverter such that the flow diverter is disposed inside of the interior lumen.

9. The ablation electrode according to claim 1, wherein an average diameter of each of the multiple narrower channels is between 5 and 50 microns.

10. The ablation electrode according to claim 1, wherein an average narrower-channel diameter of each of the multiple narrower channels is less than 50% of an average wider-channel diameter of each of the wider channels.

11. The ablation electrode according to claim 1, wherein a thickness of the flexible electrically-insulating substrate is between 5 and 75 microns.

12. The ablation electrode according to claim 1, further comprising one or more electrically-conductive traces disposed on the inner surface and electrically isolated from the inner layer,
    wherein the flexible electrically-insulating substrate is shaped to define respective holes opposite the traces, and
    wherein the outer layer comprises:
        a main portion; and
        one or more islands that are electrically isolated from the main portion and contact the traces, respectively, by virtue of at least partially filling the holes.

13. The ablation electrode according to claim 1,
wherein the outer layer comprises a conductive path on the outer surface between and joining the columns, and
wherein the inner layer comprises a conductive path on the inner surface between and joining the columns.

14. The ablation electrode according to claim 1, wherein the support structure is formed from a metallic sheet.

15. The ablation electrode according to claim 1, wherein the dome shaped distal portion comprises a central hub and a plurality of spokes that radiate from the central hub.

* * * * *